United States Patent
Watanabe

(10) Patent No.: US 11,576,587 B2
(45) Date of Patent: Feb. 14, 2023

(54) ESTIMATING THE SLEEP STATE OF A USER BASED ON BLOOD FLOW INFORMATION

(71) Applicant: KYOCERA Corporation, Kyoto (JP)

(72) Inventor: Takahiro Watanabe, Yokohama (JP)

(73) Assignee: KYOCERA Corporation, Kyoto (JP)

( * ) Notice: Subject to any disclaimer, the term of this patent is extended or adjusted under 35 U.S.C. 154(b) by 294 days.

(21) Appl. No.: 16/958,601

(22) PCT Filed: Dec. 27, 2018

(86) PCT No.: PCT/JP2018/048349
§ 371 (c)(1),
(2) Date: Jun. 26, 2020

(87) PCT Pub. No.: WO2019/131958
PCT Pub. Date: Jul. 4, 2019

(65) Prior Publication Data
US 2020/0352457 A1 Nov. 12, 2020

(30) Foreign Application Priority Data
Dec. 28, 2017 (JP) .............................. JP2017-254591

(51) Int. Cl.
*A61B 5/026* (2006.01)
*A61B 5/0285* (2006.01)
*A61B 5/00* (2006.01)

(52) U.S. Cl.
CPC .......... *A61B 5/0261* (2013.01); *A61B 5/0285* (2013.01); *A61B 5/7405* (2013.01)

(58) Field of Classification Search
None
See application file for complete search history.

(56) References Cited

U.S. PATENT DOCUMENTS

| | | | |
|---|---|---|---|
| 9,678,482 B2 | 6/2017 | Takahashi | |
| 10,335,084 B2 | 7/2019 | Inagaki et al. | |
| 2003/0235313 A1* | 12/2003 | Kurzweil | ................ A61F 11/14 381/74 |
| 2007/0249952 A1* | 10/2007 | Rubin | .................... A61M 21/00 600/544 |
| 2009/0034748 A1 | 2/2009 | Sibbald | |
| 2015/0208933 A1 | 7/2015 | Satomi et al. | |
| 2015/0350412 A1 | 12/2015 | Nagashima | |
| 2016/0217672 A1 | 7/2016 | Yoon et al. | |

(Continued)

FOREIGN PATENT DOCUMENTS

| | | |
|---|---|---|
| EP | 3689239 A1 | 8/2020 |
| JP | 2005-21331 A | 1/2005 |

(Continued)

*Primary Examiner* — Adolf Dsouza
(74) *Attorney, Agent, or Firm* — Procopio Cory Hargreaves and Savitch LLP

(57) ABSTRACT

An electronic device according to an embodiment includes a speaker capable of outputting a sound wave, a sensor capable of acquiring an optical signal related to blood flow at a measured part of a user, and a controller configured to measure blood flow information of the measured part based on the optical signal. The controller estimates a sleep state of the user based on the blood flow information and controls, based on the sleep state, a sound wave outputted from the speaker.

14 Claims, 12 Drawing Sheets

(56) References Cited

U.S. PATENT DOCUMENTS

2017/0309267 A1  10/2017  DeFranks et al.
2020/0374619 A1* 11/2020  Pergament ........... H04R 1/1041

FOREIGN PATENT DOCUMENTS

| | | |
|---|---|---|
| JP | 2005-177158 A | 7/2005 |
| JP | 2009-532926 A | 9/2009 |
| JP | 2010-018055 A | 1/2010 |
| JP | 2014-030754 A | 2/2014 |
| JP | 2016-006957 A | 1/2016 |
| JP | 2016-13221 A | 1/2016 |
| JP | 2016-55155 A | 4/2016 |
| WO | 2014/210588 A1 | 12/2014 |
| WO | 2015/194163 A1 | 12/2015 |

* cited by examiner

ESTIMATING THE SLEEP STATE OF A USER BASED ON BLOOD FLOW INFORMATION

CROSS-REFERENCE TO RELATED APPLICATION

The present application claims priority to and the benefit of Japanese Patent Application No. 2017-254591 filed Dec. 28, 2017, the entire contents of which are incorporated herein by reference.

TECHNICAL FIELD

The present disclosure relates to an electronic device, a control system, a control method, and a control program.

BACKGROUND

There is known a vehicle occupant awakening apparatus for operation control of an awakening device to awaken an occupant of a vehicle based on the sleep state of the occupant.

SUMMARY

An electronic device according to an embodiment includes a speaker capable of outputting a sound wave, a sensor capable of acquiring an optical signal related to blood flow at a measured part of a user, and a controller configured to measure blood flow information of the measured part based on the optical signal. The controller estimates a sleep state of the user based on the blood flow information and controls a sound wave outputted from the speaker based on the sleep state.

A control system according to an embodiment includes a measurement apparatus and a control apparatus. The measurement apparatus includes a speaker configured to output a sound wave and a sensor configured to acquire an optical signal related to blood flow at a measured part of a user. The control apparatus includes a controller configured to measure blood flow information of the measured part based on the optical signal. The controller estimates a sleep state of the user based on the blood flow information and controls a sound wave outputted from the speaker based on the sleep state of the user.

A control method according to an embodiment includes acquiring an optical signal related to blood flow at a measured part of a user, measuring blood flow information of the measured part based on the optical signal, estimating a sleep state of the user based on the blood flow information, performing control of a sound wave for output based on the sleep state, and outputting the sound wave based on the control.

A control program according to an embodiment is for causing a computer to acquire an optical signal related to blood flow at a measured part of a user, measure blood flow information of the measured part based on the optical signal, estimate a sleep state of the user based on the blood flow information, control a sound wave for output based on the sleep state, and output the controlled sound wave.

DETAILED DESCRIPTION

Electronic Device

Embodiment

Figure 1:
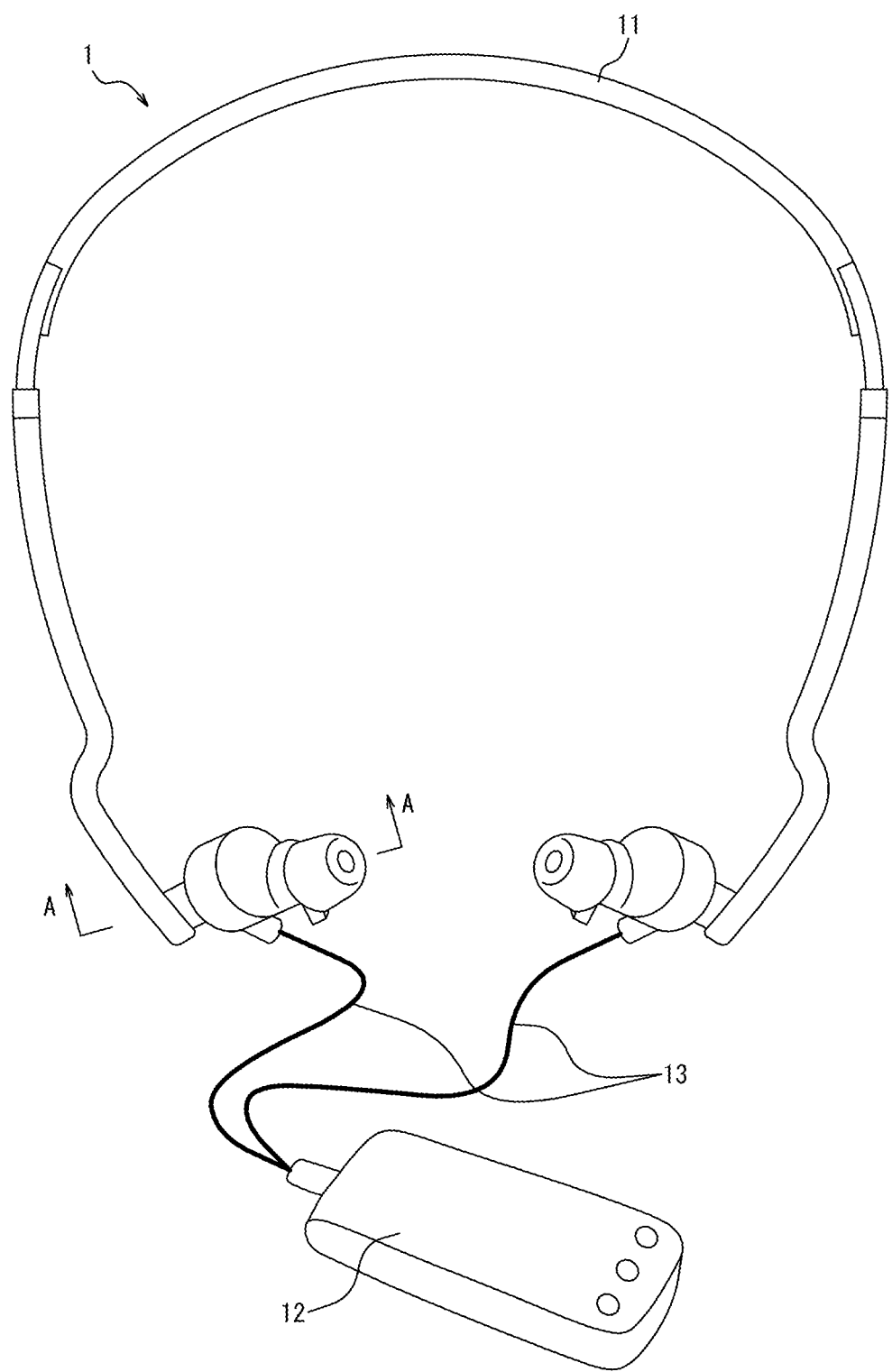
FIG. 1 schematically illustrates the appearance of an electronic device according to an embodiment.
Figure 2:
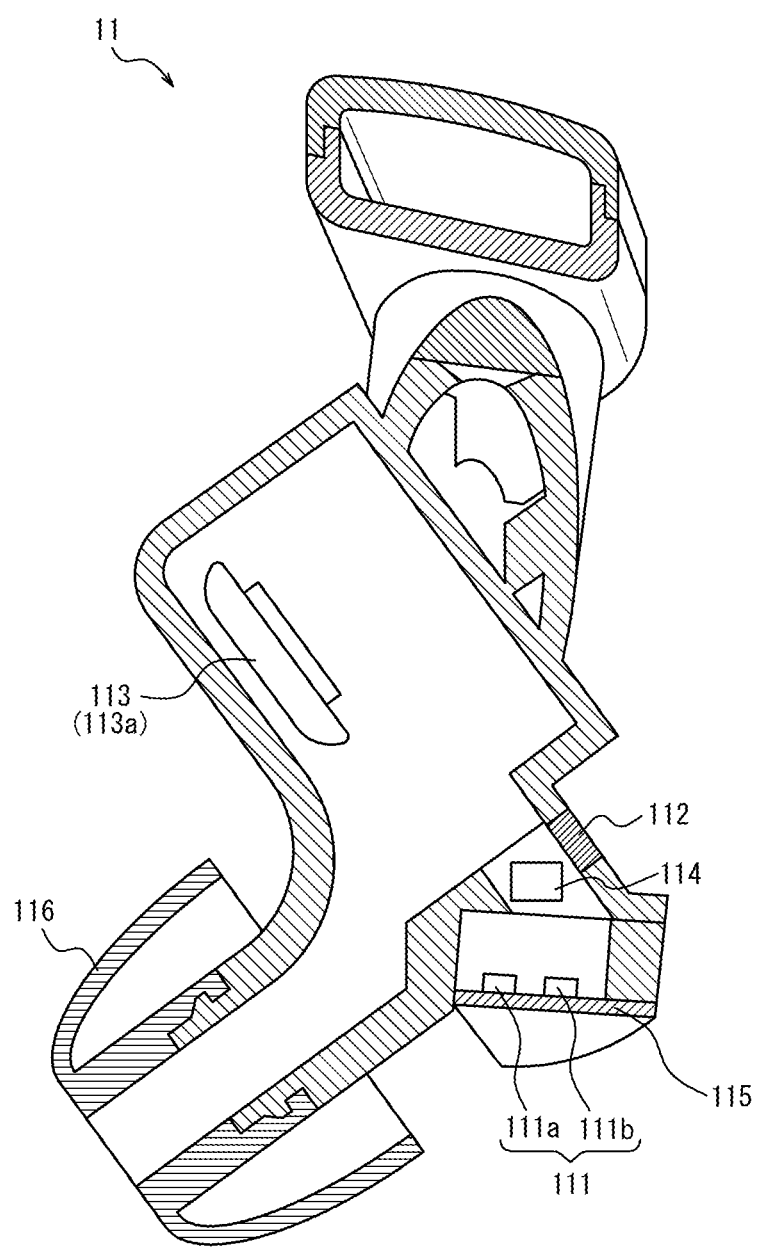
FIG. 2 is an A-A cross-section of a measurement apparatus of the electronic device of FIG. 1.
Figure 3:
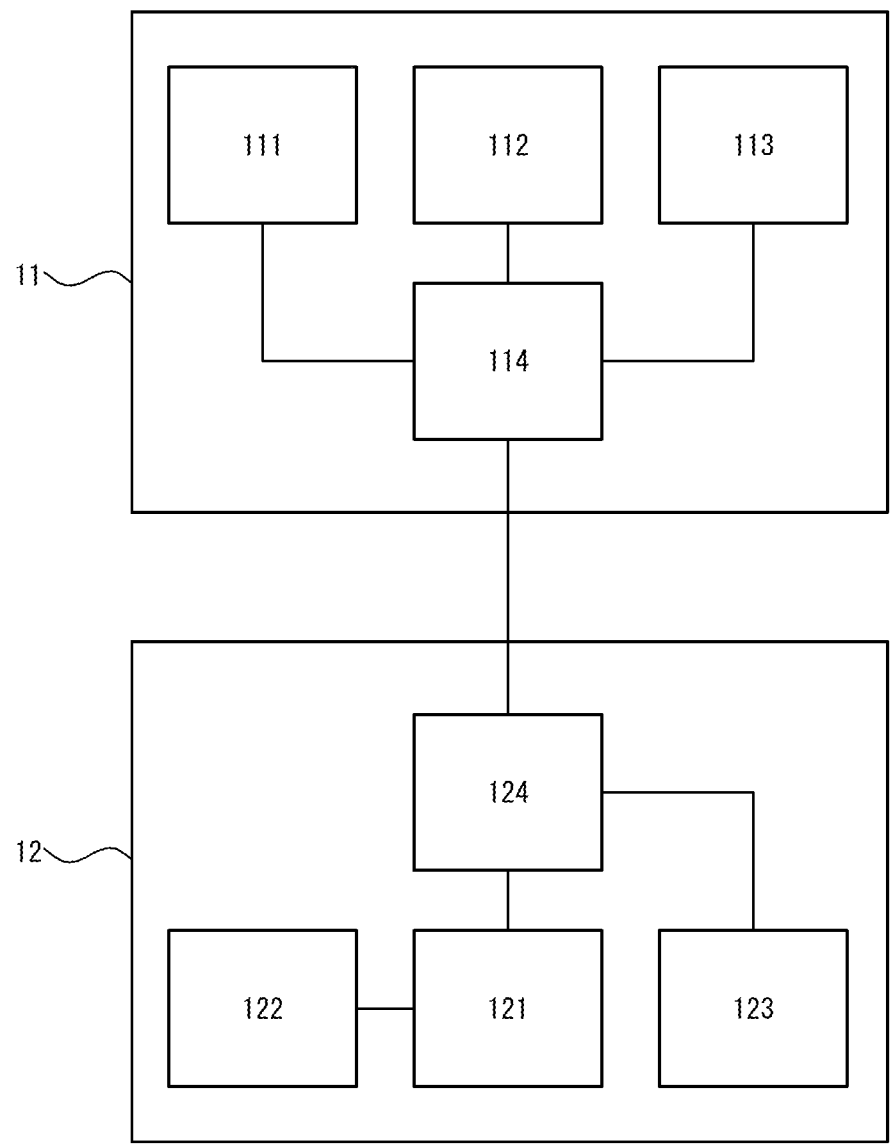
FIG. 3 is a block diagram representing functional components of the electronic device of FIG. 1.

FIG. 1 schematically illustrates the appearance of an electronic device 1 according to an embodiment. FIG. 2 is an A-A cross-section of a measurement apparatus 11 of FIG. 1. FIG. 3 is a block diagram representing the functional components of the measurement apparatus 11 and a control apparatus 12 of the electronic device 1. In FIG. 2, details of the internal mechanism of the measurement apparatus 11 are partially omitted.

The electronic device according to the present disclosure enables control of a sound wave for output based on information (blood flow information) related to blood flow of a measured part of a user. Specifically, the electronic device can estimate a sleep state of the user based on the blood flow information and can adjust an outputted sound wave in accordance with the sleep state.

The measured part where the electronic device performs measurement is an ear of the user. Specifically, the measured part is the concha of the user.

The electronic device 1 includes a measurement apparatus 11 and a control apparatus 12. The measurement apparatus 11 can measure a measured part of the user and acquire various information related to the measured part as an electric signal. A controller 121 can measure blood flow information based on the electric signal acquired by the measurement apparatus 11. The control apparatus 12 can execute various control of the electronic device 1 based on the blood flow information. The measurement apparatus 11 and the control apparatus 12 are communicatively connected by a cable 13 and can transmit and receive various signals, power, and the like. The measurement apparatus 11 and the control apparatus 12 may be communicatively connected in a wireless manner or in a combination of a wired manner and a wireless manner. The electronic device 1 can be manufactured by a well-known method.

The blood flow information measured by the electronic device is, for example, a blood flow rate, blood flow wave height, heartbeat interval, volume pulse wave, or acceleration pulse wave. The blood flow rate is the rate of the blood flow per unit time at a measured part. The blood flow wave height is the difference between the maximum and minimum values of the blood flow rate during one heartbeat and serves as an index of vasodilatation. The heartbeat interval is the interval between heartbeats and serves as an index of whether the user is relaxed. The volume pulse wave is a waveform representation of the change in blood flow rate due to a heartbeat. The volume pulse wave serves as an index of blood vessel expansion and contraction. The acceleration pulse wave is a waveform representation of the value obtained as the second derivative, with respect to time, of the blood flow rate represented as the volume pulse wave.

The measurement apparatus 11 of the electronic device 1 includes a sensor 111, a microphone 112, a speaker 113 (a notification interface 113a), and a communication interface 114.

The sensor 111 of the measurement apparatus 11 can transmit and receive optical signals. The sensor 111 includes an optical emitter 111a and an optical detector 111b. The optical emitter 111a can irradiate light onto the measured part. The optical receiver 111b can receive interference light that includes light, from among the light irradiated by the optical emitter 111a, scattered at the measured part.

It suffices for the light irradiated by the optical emitter 111a to be light of a wavelength capable of detecting a predetermined component included in blood. For example, in the case of measuring blood flow, the wavelength of light irradiated by the optical emitter 111a is, for example, 600 nm to 900 nm. The optical emitter 111a is, for example, configured by one laser diode (LD).

The optical detector 111b can convert a detected optical signal to an electric signal and transmit the electric signal to the control apparatus 12. The optical detector 111b is, for example, configured by at least one photodiode (PD).

An optical detector capable of detecting light of a wavelength corresponding to the purpose of measurement is used as the optical detector 111b. Specifically, the optical detector 111b is capable of detecting interference light produced by light with no Doppler shift, such as scattered light from a still object, and scattered light that has experienced a Doppler shift due to a moving object. The optical detector 111b can output the beat of the interference light as an electric signal. The electric signal of the beat (beat signal) is the relationship between the intensity of the beat and time. It suffices for the optical detector 111b of the present disclosure, however, to have a time resolution capable of following fluctuations in the intensity of the beat. In the case of measuring blood flow, the still object is body tissue such as skin, and the moving object is blood.

The microphone 112 of the measurement apparatus 11 can collect an ambient sound wave as a sound signal. The microphone 112 can convert the sound signal to an electric signal and transmit the electric signal to the control apparatus 12. The microphone 112 can be manufactured by a well-known method.

The speaker 113 of the measurement apparatus 11 can convert the electric signal inputted from the control apparatus 12 to a sound signal and output a sound wave. The speaker 113 can be manufactured by a well-known method.

The communication interface 114 of the measurement apparatus 11 can transmit and receive various signals by communicating with the control apparatus 12. Specifically, the communication interface 114 can, for example, transmit the electric signal yielded by conversion of the optical signal acquired by the optical detector 111b and the electric signal yielded by conversion of the sound signal acquired by the microphone 112 to the control apparatus 12. The communication interface 114 can receive, from the control apparatus 12, a signal for causing the sensor 111 to execute measurement processing and a signal for causing the speaker 113 to output a sound wave, for example. The communication interface 114 communicates with the control apparatus 12 by any combination of wired and wireless communication. The communication interface 114 can be manufactured by a well-known method.

The measurement apparatus 11 further includes a case 115 and an earpiece 116. The case 115 can protect components disposed therein. The earpiece 116 can be inserted in the external ear canal of the user and can maintain a contact state between the measurement apparatus 11 and the measured part. The case 115 is, for example, made of synthetic resin, metal, or the like. The earpiece 116 is made of resin, such as silicone.

The sensor 111 of the measurement apparatus 11 is provided at a position that comes into contact with the measured part. Specifically, the sensor 111 is provided in the case 115 at a position that comes into contact with the measured part when the earpiece 116 is inserted into the external ear canal. The case 115 can function as a protective member of the sensor 111.

The control apparatus 12 of the electronic device 1 includes a controller 121, a storage 122, an input interface 123, and a communication interface 124.

The controller 121 of the control apparatus 12 can control the electronic device 1. While not illustrated, the controller 121 includes at least one processor that, starting with the functional blocks of the electronic device 1, controls and manages the electronic device 1 overall. The functions of the controller 121 can be implemented by a processor, such as a central processing unit (CPU), that executes programs with prescribed control procedures. Such programs may, for example, be stored in the storage 122, on an external storage medium connected to the electronic device 1, or the like.

The processor may, for example, be implemented as a single integrated circuit (IC) or a plurality of communicatively connected ICs and/or discrete circuits. Specifically, the processor may include one or more circuits or units configured to execute one or more data calculation procedures or processes by executing instructions stored in related memory, for example. The processor may be firmware (for example, a discrete logic component) configured to execute one or more data calculation procedures or processes.

The processor may, for example, include one or more processors, controllers, microprocessors, microcontrollers, application-specific integrated circuits (ASIC), digital signal processing apparatuses, programmable logic devices, field programmable gate arrays, any combination of these devices or configurations, or any combination of other known devices or configurations.

The storage 122 can be configured by a semiconductor memory, a magnetic memory, or the like. The storage 122 can, for example, store various information and/or programs for operating the electronic device 1. The storage 122 may also function as a working memory.

The input interface 123 can input information (operation information) related to operation of the electronic device 1 to the controller 121 based on user operation. The input interface 123 may, for example, be configured using operation buttons (operation keys), a touchscreen, or the like. The operation information is, for example, to start and stop measurement, to set an alarm, to set a timer, or the like.

The communication interface 124 can communicate with the communication interface 114 of the measurement apparatus 11 to transmit and receive various signals. In the electronic device according to an embodiment, the communication interface 114 of the measurement apparatus 11 and the communication interface 124 of the control apparatus 12 can communicate via the cable 13. The communication interface 124 can, for example, receive the electric signal yielded by conversion of the optical signal acquired by the optical detector 111b and the electric signal yielded by conversion of the sound signal acquired by the microphone 112 from the measurement apparatus 11. The communication interface 124 can transmit, to the measurement apparatus 11, a signal for causing the sensor 111 to execute measurement processing and a signal for causing the speaker 113 to output a sound wave. The communication interface 124 may communicate with the measurement apparatus 11 by any combination of wired and wireless communication.

The controller 121 can measure blood flow information using the Doppler effect of light. Specifically, the controller 121 can measure blood flow information at the measured part of the user based on the optical signal acquired by the measurement apparatus 11.

When irradiated light is scattered by flowing blood in body tissue, the frequency shifts due to the Doppler effect (Doppler shift) in accordance with the flow rate or flow speed of blood. The Doppler effect can therefore be used to measure blood flow information.

The controller 121 performs a Fast Fourier Transform (FFT) on the beat signal acquired by the optical detector 111b to acquire the relationship between the frequency of output of the optical detector 111b and a weighted frequency (frequency intensity) as a frequency spectrum. The frequency intensity fluctuates in the frequency spectrum in accordance with a change in the amount of flowing blood. Accordingly, the controller 121 can measure blood flow information based on the frequency intensity of the frequency spectrum. Specifically, blood flow information can be measured based on the result of integrating the product of the frequency and frequency intensity of the frequency spectrum over an arbitrary frequency range.

Figure 4:
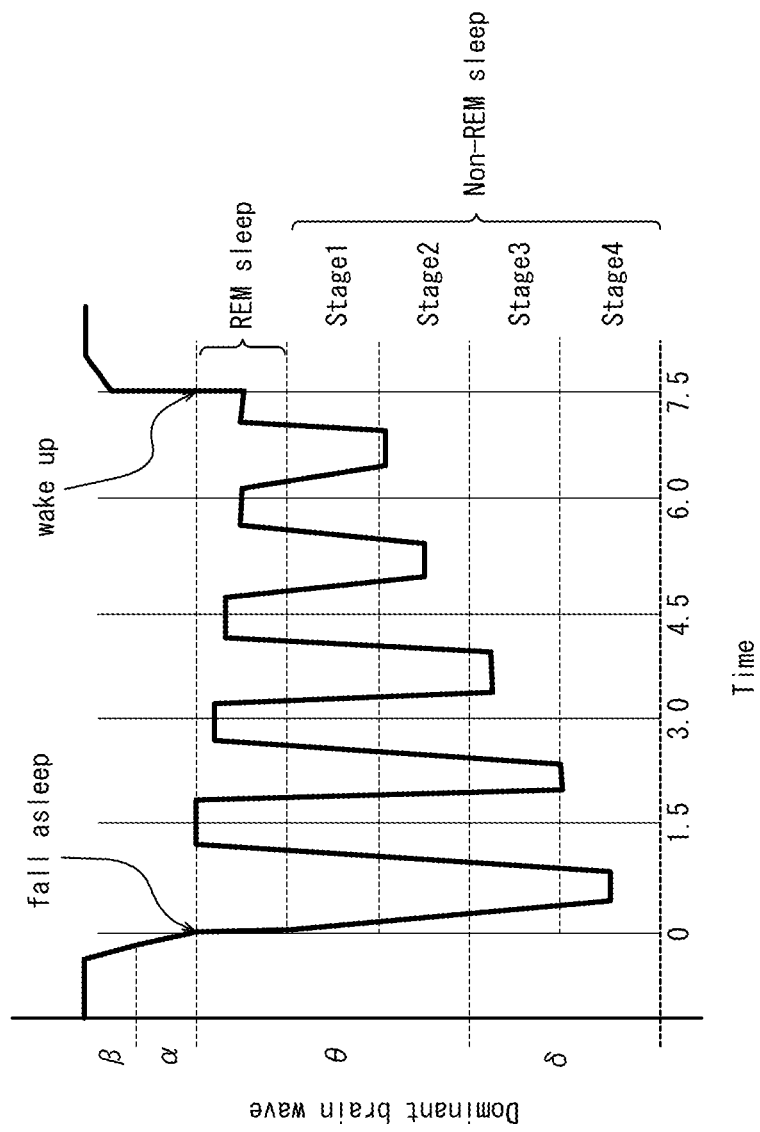
FIG. 4 schematically represents an example of the transition of sleep-related brain waves.

FIG. 4 schematically illustrates an example of sleep-related brain waves. FIG. 4 illustrates the change in sleep-related brain waves and the dominant brain waves.

The controller 121 can estimate the sleep state of the user based on the measured blood flow information. The sleep state can be classified by brain waves, for example.

Brain waves are divided into four types, starting from longer wavelength: β waves, α waves, θ waves, and δ waves. β waves are, for example, brain waves in a frequency range of 38 Hz to 14 Hz. α waves are, for example, brain waves in a frequency range of 14 Hz to 8 Hz. θ waves are, for example, brain waves in a frequency range of 8 Hz to 4 Hz. δ waves are, for example, brain waves in a frequency range of 4 Hz to 0.5 Hz.

When θ waves and δ waves are dominant compared to β waves and a waves, people are asleep. Here, "dominant" refers to a large ratio of certain waves among measured brain waves. It is known that dominant brain waves change cyclically in the range of θ waves and δ waves during sleep (FIG. 4). Furthermore, people are in rapid eye movement (REM) sleep when the ratio of θ waves included in brain waves is less than a predetermined ratio and are in non-rapid eye movement (non-REM) sleep when the ratio of θ waves is equal to or greater than a predetermined ratio and when δ waves are dominant (FIG. 4).

REM sleep is sleep with rapid eye movements. Non-REM sleep is sleep without rapid eye movements.

Non-REM sleep is further classified by the depth of sleep. Non-REM sleep may be classified in order of increasing depth as stage 1, stage 2, stage 3, and stage 4.

The controller 121 can use the relationship between blood flow and sleep state to estimate the above-described sleep state based on the blood flow information. Specifically, the controller 121 can estimate the sleep state based on the blood flow information by using the bodily characteristic of how blood flow increases at the onset of sleep and decreases as sleep deepens. The controller 121 of the electronic device 1 according to an embodiment can estimate the sleep state of the user based on the blood flow.

Figure 5:
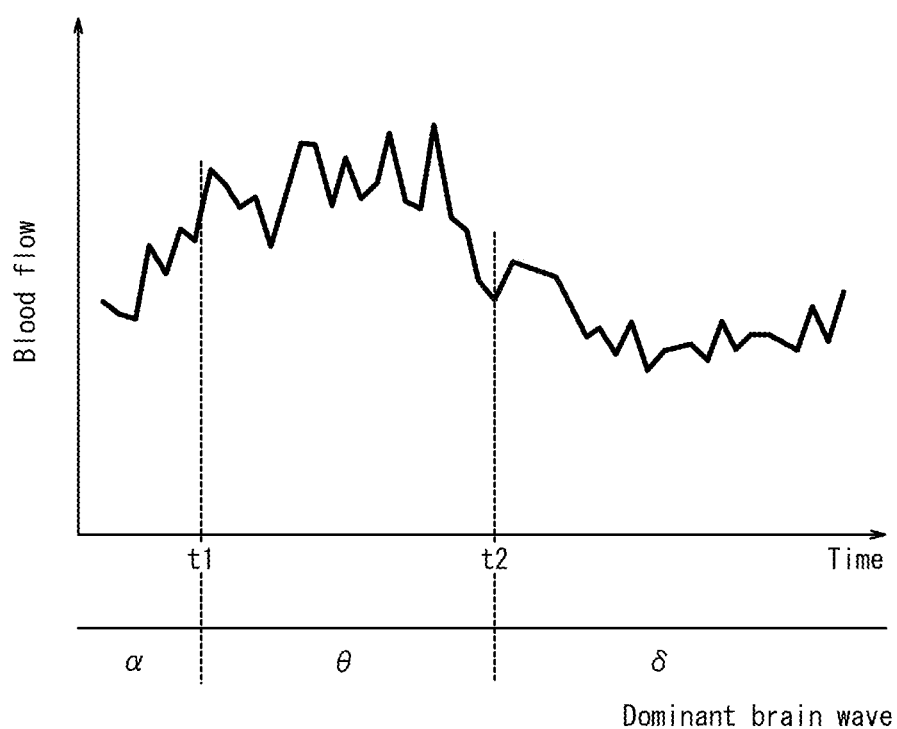
FIG. 5 schematically represents an example of the transition of sleep-related blood flow.

FIG. 5 schematically represents the transition of sleep-related blood flow. The dominant brain waves are also indicated in FIG. 5 for reference.

Since the blood flow increases at the onset of sleep, the controller 121 can estimate that the user has fallen asleep when the blood flow exceeds a predetermined threshold (first threshold). In FIG. 5, the blood flow exceeds the first threshold at t1. The controller 121 can therefore estimate that the user has fallen asleep at t1. The controller 121 can also estimate that the user is awake during the time until t1 and can estimate that the user is sleeping lightly from time t1 onward.

The blood flow decreases as sleep deepens. Therefore, the controller 121 can estimate that the user has gone from light sleep to deep sleep when the blood flow becomes equal to or less than a predetermined threshold (second threshold). In FIG. 5, the blood flow becomes equal to or less than the second threshold at t2. The controller 121 can therefore estimate that the user has gone from light sleep to deep sleep at t2. The controller 121 can also estimate that the user is sleeping lightly during the time from t1 to t2 and can estimate that the user is sleeping deeply from time t2 onward.

When sleeping, the user repeats a cycle of light sleep and deep sleep. When the blood flow again reaches the second threshold after t2, the controller 121 may therefore estimate that the user has gone from deep sleep to light sleep. When the blood flow again reaches the first threshold, the controller 121 may estimate that the user has awakened.

The first threshold and the second threshold are set in advance and stored in the storage 122. Specifically, the controller 121 may, for example, measure the blood flow of the user at bedtime in advance and use the measurement result to set the first threshold and the second threshold. The controller 121 may similarly set a threshold for estimating that the user has gone from deep sleep to light sleep and a threshold for estimating that the user has awakened.

Here, when the user awakens from a deep sleep, the user tends to be sleepy or very lethargic immediately after awakening and to have poor brain activity (sleep inertia). The user's work efficiency dramatically decreases in this case. The user may unintentionally awaken from sleep, however, due to ambient sound or some sort of noise.

To address this issue, the controller 121 of the electronic device 1 can control the sound wave outputted from the speaker 113 based on the sleep state of the user and an ambient sound wave. Specifically, the controller 121 can perform control for the speaker 113 to output a sound wave that decreases the ambient sound wave. Consequently, the electronic device 1 can reduce the effect of ambient sound, noise, or the like on sleep and can therefore improve the quality of the user's sleep.

Figure 6:
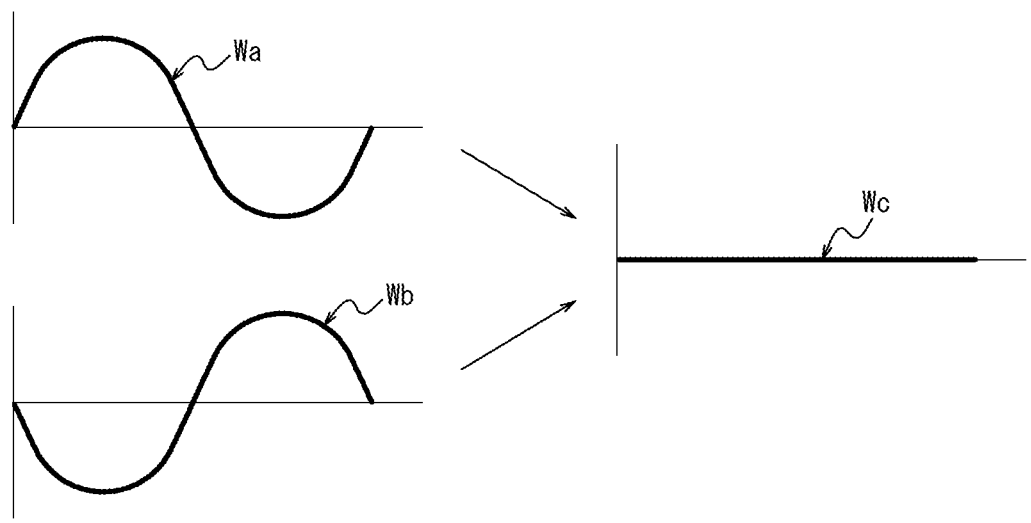
FIG. 6 illustrates the principle of noise canceling.

FIG. 6 represents a sound wave outputted by the speaker 113 of the electronic device 1 according to an embodiment.

The controller 121 can perform control so that the sound wave outputted from the speaker 113 has opposite phase from the ambient sound wave collected by the microphone 112. By outputting a sound wave with opposite phase from the ambient sound wave, the electronic device 1 can reduce the amount of ambient sound, noise, and the like that the user can hear. Consequently, the electronic device 1 can reduce the probability of the user unintentionally awakening.

In FIG. 6, the waveform representing the ambient sound wave is waveform Wa, and the waveform representing the sound outputted by the speaker 113 is waveform Wb. The waveform yielded by combining the waveforms Wa and Wb is waveform Wc. When a sound wave with the waveform Wb of opposite phase is overlaid on a sound wave with the waveform Wa, the waveforms Wa and Wb cancel each other due to the nature of sound, yielding a sound wave represented by the waveform Wc. In other words, the electronic device 1 can cancel or reduce an ambient sound wave by overlaying a sound wave of opposite phase on the ambient sound wave.

The controller 121 can use this property to cause the speaker 113 to function as a noise canceller. Specifically, the controller 121 first analyzes the ambient sound wave collected by the microphone 112. Next, the controller 121 generates a sound signal for outputting a sound wave of opposite phase from the ambient sound wave. The controller 121 then transmits the generated sound wave to the measurement apparatus 11 and controls the speaker 113 to output the sound wave of opposite phase. Consequently, the ambient sound wave is canceled or reduced.

The user can fall asleep more easily as a result of the controller 121 causing the speaker 113 to function as a noise canceller before the user falls asleep. When the controller 121 causes the speaker 113 to function as a noise canceller while the user is asleep, the user's sleep is also less likely to be disturbed. In other words, this control by the controller 121 of the electronic device 1 makes the user less likely to awaken, thereby improving the quality of the user's sleep.

The controller 121 can determine the timing for awakening the user based on the estimated sleep state. For example, the controller 121 can determine that the time when the user is sleeping lightly is the timing for awakening the user. Specifically, the controller 121 can determine that the time between t1 and t2 in FIG. 5, for example, is the timing for awakening. This makes the user less likely to suffer sleep inertia. The electronic device 1 can therefore improve the quality of the user's sleep. Even after t2, the controller 121 may determine that a time when the user is sleeping lightly again is the timing for awakening the user.

The controller 121 can perform control for the speaker 113 to output a sound wave of opposite phase from the ambient sound wave until determining that the timing for awakening the user has been reached. Consequently, the electronic device 1 can reduce the probability of the user unintentionally awakening and can therefore improve the quality of the user's sleep. In other words, the controller 121 does not output a sound wave of opposite phase from the ambient sound wave at the timing for awakening the user. This makes it easier for the user to awaken when he should. The electronic device 1 can therefore improve convenience.

Figure 7A:
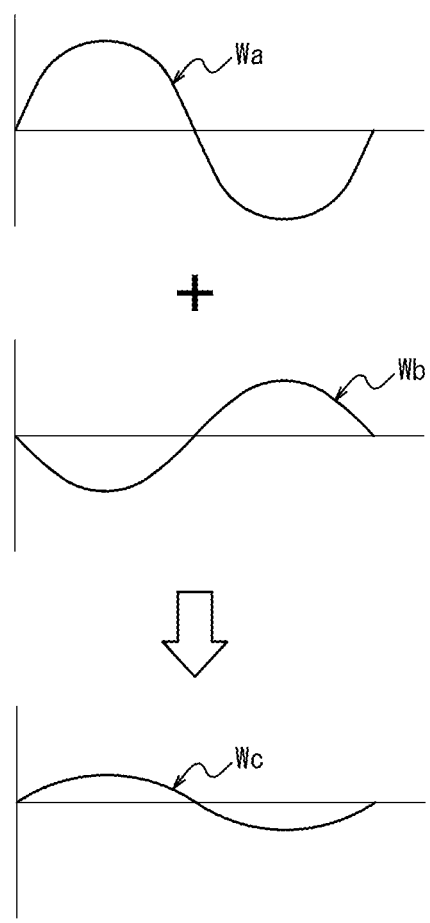
FIG. 7A illustrates a sound wave outputted by the speaker of the electronic device of FIG. 1.
Figure 7B:
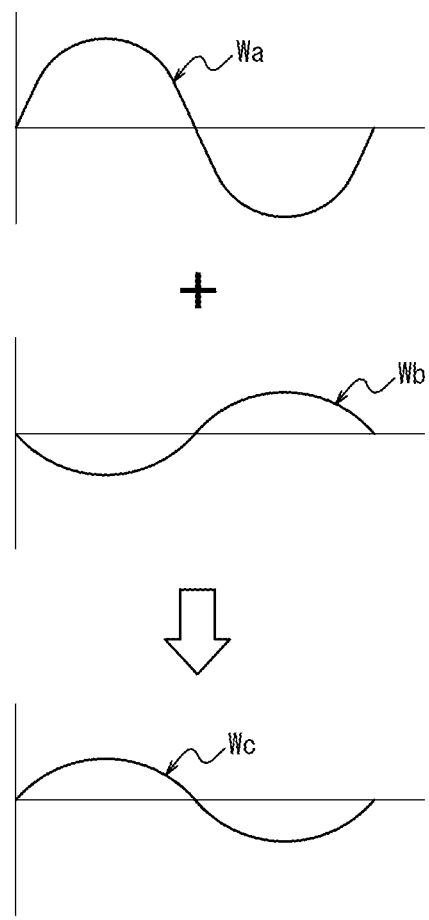
FIG. 7B illustrates a sound wave outputted by the speaker of the electronic device of FIG. 1.
Figure 7C:
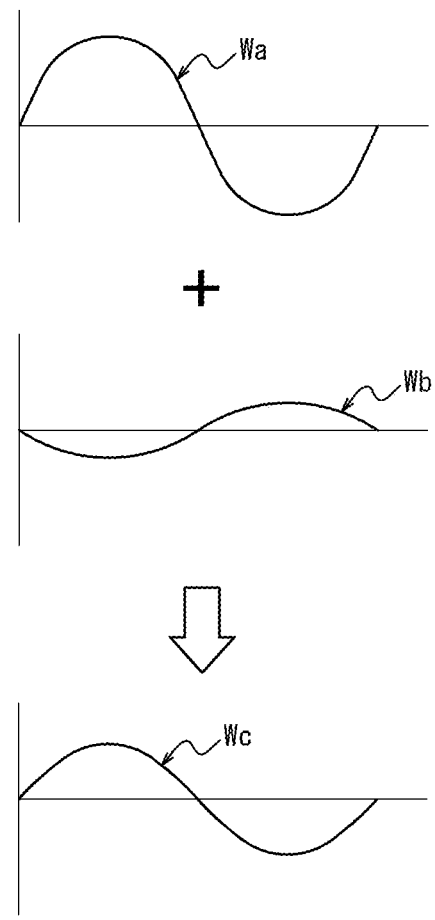
FIG. 7C illustrates a sound wave outputted by the speaker of the electronic device of FIG. 1.

FIGS. 7A through 7C represent sound waves outputted from the speaker 113. In FIGS. 7A through 7C, waveform Wa indicates the waveform representing an ambient sound wave, and waveform Wb indicates the waveform representing a sound wave outputted from the speaker 113. Waveform Wc indicates the waveform representing the sound wave that reaches the user's ears.

The controller 121 can control the intensity of the sound wave outputted from the speaker 113 based on the estimated sleep state. Specifically, the controller 121 can output a sound wave with the same intensity as the ambient sound wave collected by the microphone 112 while the user is sleeping. The ambient sound wave is ideally canceled out as a result. The electronic device 1 therefore makes the user's sleep less likely to be disturbed.

The controller 121 can gradually weaken the sound wave of opposite phase outputted from the speaker 113 after determining that the timing for awakening the user has been reached. In other words, after determining that the timing for awakening the user has been reached, the controller 121 can perform control to weaken the noise canceling function gradually. The sound reaching the user's ear therefore gradually increases. Consequently, the electronic device 1 can reduce the stress felt by the user as compared to when a loud ambient sound wave suddenly becomes audible at the timing of awakening.

The controller 121 may perform control so that the sound wave outputted from the speaker 113 becomes weaker continuously. Consequently, the electronic device 1 can reduce the user's discomfort regarding the way he hears the sound wave due to a change in the noise canceling effect.

The controller 121 may also perform control so that the sound wave outputted from the speaker 113 becomes weaker in a stepwise manner. Consequently, the electronic device 1 can save energy by reducing the number of times the voltage changes.

The controller 121 may perform control so that the sound wave stops being outputted from the speaker 113 upon a predetermined time elapsing after the determination that the timing for awakening the user has been reached. This makes it easier to align the timing at which the user awakens. The electronic device 1 can therefore improve convenience.

Figure 8:
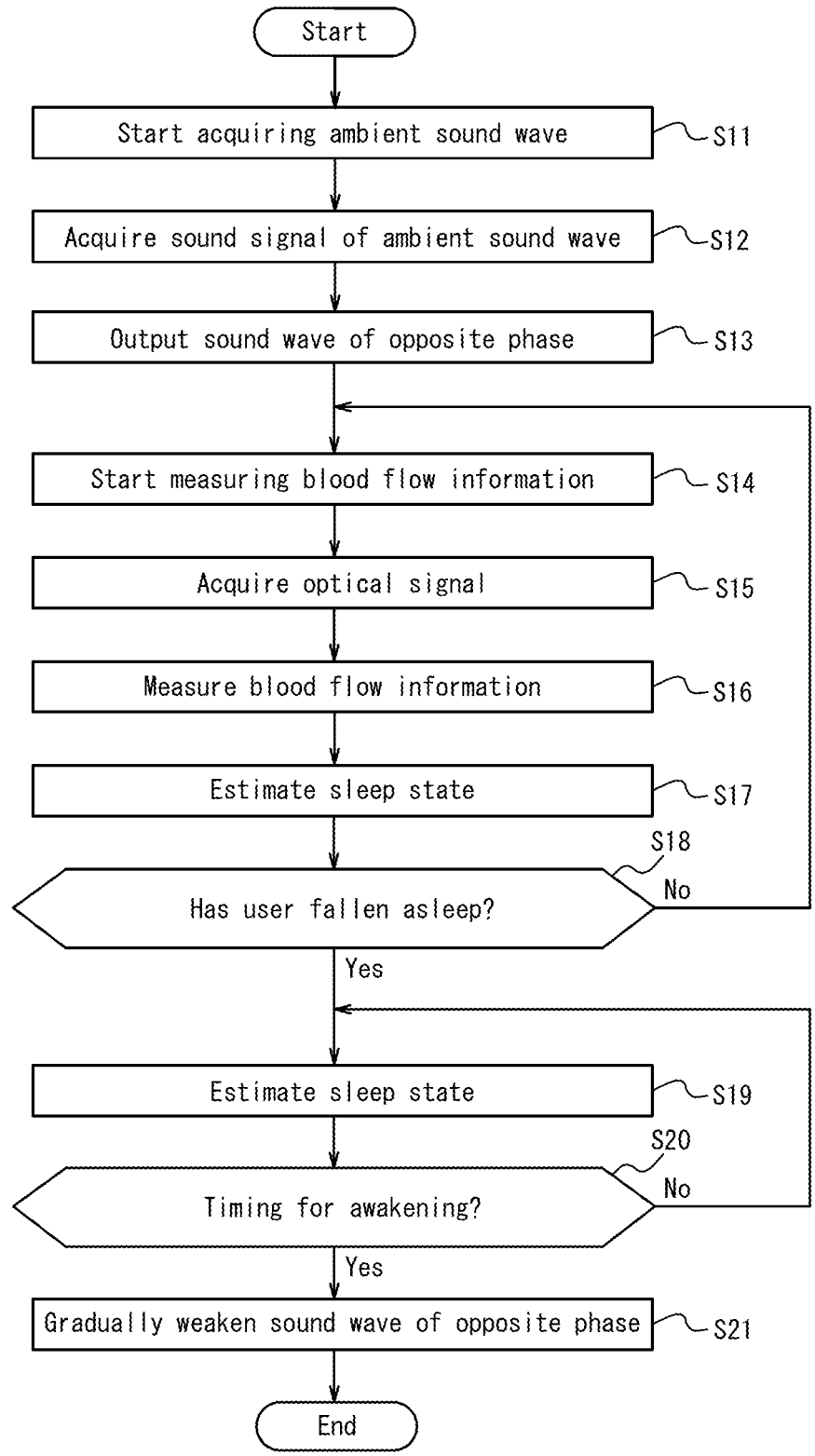
FIG. 8 is a flowchart illustrating an example of processing executed by the electronic device of FIG. 1.

FIG. 8 is a flowchart illustrating an example of processing executed by the controller 121. The flowchart in FIG. 8 begins when, for example, the user wears the measurement apparatus 11 and uses the input interface 123 of the control apparatus 12 to perform an operation for starting processing.

Next, the controller 121 controls the microphone 112 of the measurement apparatus 11 to start collecting an ambient sound wave (step S11). The controller 121 acquires a sound signal of the ambient sound wave collected by the microphone 112 (step S12).

Next, the controller 121 analyzes the acquired sound signal and performs control for the speaker 113 to output a sound wave of opposite phase from the ambient sound wave (step S13).

The controller 121 controls the sensor 111 of the measurement apparatus 11 to start measuring the blood flow information of the user (step S14).

Next, the controller 121 acquires an optical signal acquired by the optical detector 111b (step S15). The controller 121 then measures the blood flow information of the user based on the acquired optical signal (step S16).

Next, the controller 121 estimates the sleep state of the user based on the measured blood flow information (step S17). The controller 121 then determines whether the user has fallen asleep based on the estimated sleep state (step S18).

When it is determined that the user has not fallen asleep (step S18: No), the controller 121 transitions to step S14 and repeats steps S14 through S18 until determining that the user has fallen asleep.

When it is determined that the user has fallen asleep (step S18: Yes), the controller 121 measures the blood flow information of the user and estimates the sleep state of the user based on the blood flow information as in steps S14 to S17 (step S19).

Next, the controller 121 determines whether the timing for awakening the user has been reached based on the sleep state estimated in step S19 (step S20).

When it is determined that the timing for awakening the user has not been reached (step S20: No), the controller 121 transitions to step S19 and continually estimates the sleep state of the user until determining that the timing for awakening has been reached.

When it is determined that the timing for awakening the user has been reached (step S20: Yes), the controller 121 performs control to gradually weaken the sound wave, outputted from the speaker 113, of opposite phase from the ambient sound wave (step S21).

Other Embodiment

A speaker 113 of the electronic device 1 according to another embodiment can output a sound wave encouraging the user to awaken. Specifically, the speaker 113 can output an audible sound wave as an alarm sound to awaken the user. The alarm sound may, for example, be an alarm, music, a natural sound such as the sound of a flowing river, or the like.

The controller 121 can control the intensity of the alarm sound outputted from the speaker 113 based on the estimated sleep state. Specifically, the controller 121 can control the volume of the alarm sound outputted from the speaker 113. The electronic device 1 can thereby awaken the user more easily.

When the controller 121 determines that the timing for awakening the user has been reached based on the sleep state, the controller 121 can perform control so that the alarm sound is outputted. This makes the user less likely to suffer sleep inertia. The electronic device 1 can therefore more easily awaken the user while improving the quality of the user's sleep.

After determining that the timing for awakening the user has been reached, the controller 121 can perform control to increase the intensity of the outputted alarm sound gradually. Specifically, the controller 121 can control the volume of the alarm sound outputted from the speaker 113 to increase gradually. Consequently, the electronic device 1 can reduce the stress felt by the user as compared to when a loud sound is suddenly outputted at the timing of awakening.

Figure 9:
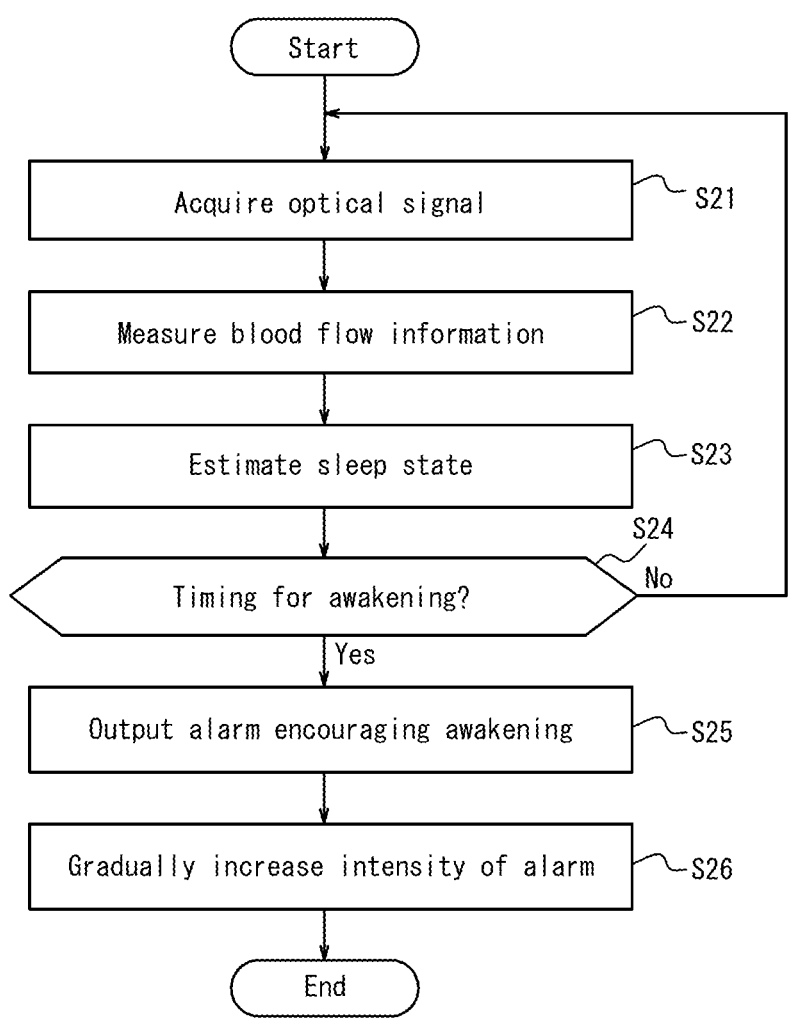
FIG. 9 is a flowchart illustrating an example of processing executed by an electronic device according to another embodiment.

FIG. 9 is a flowchart illustrating an example of processing executed by the controller 121 according to the present embodiment. The controller 121 may execute the processing of FIG. 9 after determining that the user has fallen asleep based on the blood flow. It is assumed that at the start of the processing of FIG. 9, the sensor 111 is activated, and the controller 121 has started measuring the blood flow information.

First, the controller 121 acquires an optical signal acquired by the optical detector 111b (step S21). The controller 121 then measures the blood flow information of the user based on the acquired optical signal (step S22).

Next, the controller 121 estimates the sleep state of the user based on the measured blood flow information (step S23). The controller 121 then determines whether the timing for awakening the user has been reached based on the estimated sleep state (step S24).

When it is determined that the timing for awakening the user has not been reached (step S24: No), the controller 121 transitions to step S21 and continually executes steps S21 to S24 until determining that the timing for awakening has been reached.

When it is determined that the timing for awakening the user has been reached (step S24: Yes), the controller 121 starts output of the alarm sound (step S25).

After it is determined that the timing for awakening the user has been reached, the controller 121 gradually increases the intensity of the alarm sound (step S26).

Various embodiments have been described for a complete and clear disclosure. The appended claims, however, are not limited to the above-described embodiments and are to be construed as encompassing all of the possible modifications and alternate configurations that a person of ordinary skill in the art could make within the scope of the fundamental features illustrated in the present disclosure. The subject matter of the various embodiments may also be freely combined.

For example, the measured part has been described as being the concha in the above embodiments, but this example is not limiting.

Specifically, the measured part may be a part that has a small shunt distribution and is not easily affected by expansion and contraction of blood vessels due to the autonomic nerves. The measured part may, for example, be the tragus.

The measured part may be a part other than the ear. For example, the measured part may be a finger, a wrist, the forehead, the tip of the nose, or the like. In other words, the measured part may be any part allowing acquisition of biological information for measuring the blood flow information.

It suffices for the speaker 113 to be capable of outputting a sound wave of opposite phase from an ambient sound wave or a sound wave for awakening the user. In other words, it suffices for the speaker 113 to be capable of implementing either a noise canceling function or an alarm function.

The electronic device 1 according to an embodiment of the present disclosure uses a sound wave to encourage the user to awaken, but this example is not necessarily limiting. In other words, the electronic device 1 may encourage the user to awaken using means other than a sound wave. Specifically, the electronic device 1 may encourage the user to awaken with a visual method based on light emission or the like, an audible method using speech or the like, a tactile method using vibration or the like, or a combination of these methods, for example. The user can thereby awaken with a method appropriate for the user, improving the convenience of the electronic device 1.

The electronic device 1 may, for example, use vibration to encourage the user to awaken. While not illustrated, the electronic device 1 may further include a vibration unit capable of generating vibration in this case. When the controller 121 determines that the timing for awakening the user has been reached based on the estimated sleep state of the user, the controller 121 can cause the vibration unit to start vibrating. The controller 121 can then gradually intensify the vibration of the vibration unit. Consequently, the electronic device 1 can reduce the stress felt by the user as compared to when an intense vibration is suddenly outputted at the timing of awakening. The electronic device 1 may use both the vibration unit and the speaker 113 to encourage the user to awaken.

In the above-described embodiments, the noise reaching the ears of the user has been described as being reduced by a sound wave of opposite phase outputted from the speaker 113. The method for reducing the noise reaching the ears of the user is not, however, limited to this example. Instead of the earpiece 116, a component capable of reducing noise may be used to reduce the noise reaching the ears of the user, for example. Specifically, earplugs may be used instead of the earpiece 116, for example. The earplugs may, in this case, have a function capable of changing the degree of noise reduction.

(Control System)

The electronic device described in the above embodiments may be interpreted as a control system. For example, the functions of the control apparatus 12 described in the above embodiments may be provided in another apparatus as one function. Specifically, the functions of the control apparatus 12 described in the above embodiments may be provided in a mobile terminal such as a smartphone. The control system can therefore increase the degree of design freedom. It suffices for this mobile terminal and the measurement apparatus 11 described in the above embodiments to be wirelessly connected to allow communication. The configuration of the control system may include components similar to those of the electronic device described above.

Figure 10:
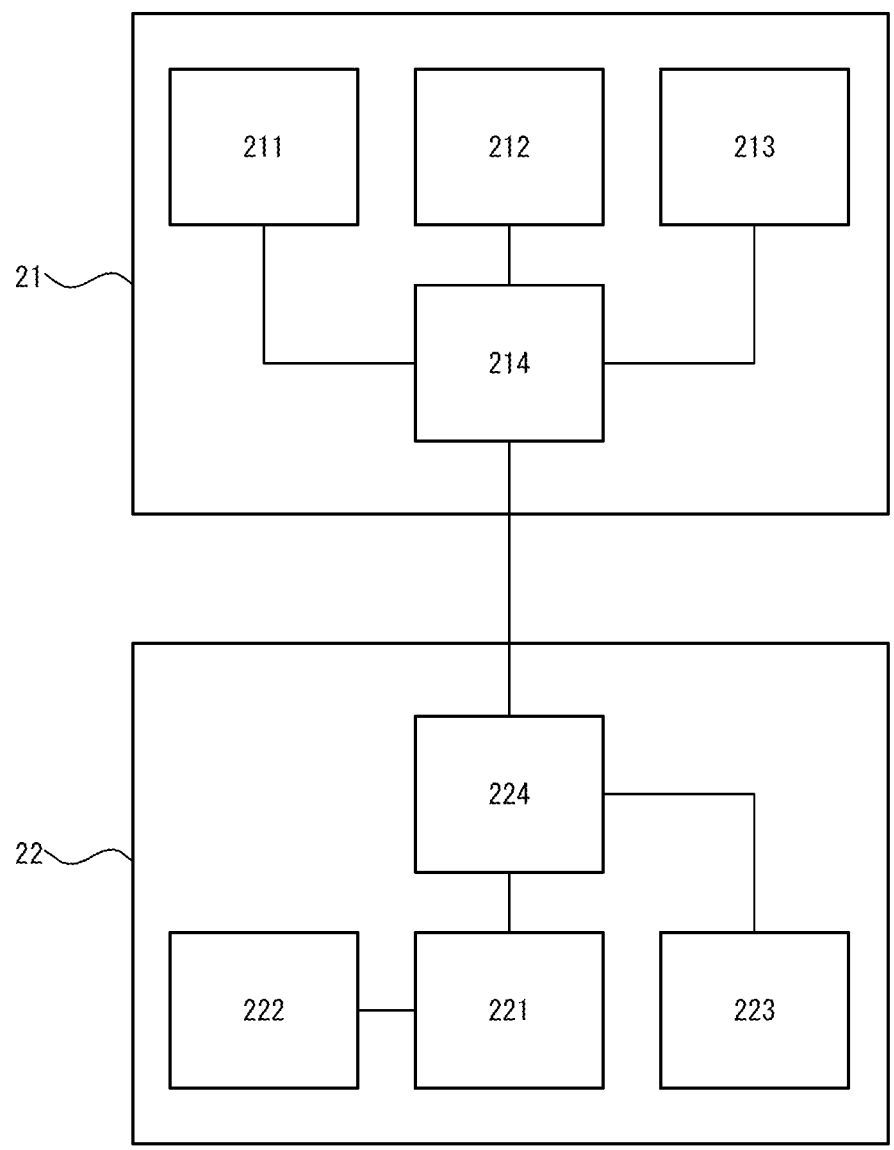
FIG. 10 is a block diagram representing functional components of a control system according to an embodiment.

FIG. 10 is a block diagram representing functional components of a control system 2 according to an embodiment.

The control system 2 according to an embodiment includes a measurement apparatus 21 and a control apparatus 22. The measurement apparatus 21 includes a speaker 213 configured to output a sound wave and a sensor 211 configured to acquire an optical signal related to blood flow at a measured part of a user. The control apparatus 22 includes a controller 221 configured to measure blood flow information of the measured part based on the optical signal. The controller 221 can estimate a sleep state of the user based on the blood flow information and control, based on the sleep state of the user, a sound wave outputted from the speaker 213.

In the control system 2, the measurement apparatus 21 may further include a microphone 212 configured to collect an ambient sound wave. The control apparatus 22 may control the sound wave outputted from the speaker 213 based on the ambient sound wave and the sleep state of the user.

In the control system 2, the control apparatus 22 may be configured to output an alarm sound from the speaker 213 to awaken the user based on the sleep state.

(Control Method)

The processing executed by the control apparatus of the electronic device described in the above embodiments may be interpreted as a control method. A control method according to an embodiment includes acquiring an optical signal related to blood flow at a measured part of a user, measuring blood flow information of the measured part based on the optical signal, estimating a sleep state of the user based on the blood flow information, performing control of a sound wave for output based on the sleep state, and outputting the sound wave based on the control.

The control method may further include acquiring an ambient sound wave and performing control of a sound wave for output based on the ambient sound wave and the sleep state.

The control method may further include outputting an alarm sound to awaken the user based on the sleep state.

(Control Program)

The processing executed by the control apparatus of the electronic device described in the above embodiments may be interpreted as a control program. A control program according to an embodiment is for causing a computer to acquire an optical signal related to blood flow at a measured part of a user, measure blood flow information of the measured part based on the optical signal, estimate a sleep state of the user based on the blood flow information, control a sound wave for output based on the sleep state, and output the controlled sound wave.

The control program may further cause the computer to collect an ambient sound wave and control a sound wave for output based on the ambient sound wave and the sleep state.

The control program may further cause the computer to output an alarm sound to awaken the user based on the sleep state.

The invention claimed is:

1. An electronic device comprising:
    a speaker capable of outputting a sound wave;
    a sensor capable of acquiring an optical signal related to blood flow at a measured part of a user; and
    a controller configured to measure blood flow information of the measured part based on the optical signal, to estimate a sleep state of the user based on the blood flow information, and to control a sound wave outputted from the speaker based on the sleep state,
    a microphone capable of collecting an ambient sound wave;
    wherein the controller is configured to control the sound wave outputted from the speaker based on the ambient sound wave and the sleep state, wherein the sound wave outputted from the speaker is a sound wave of opposite phase from the ambient sound wave; and
    wherein the controller is configured to perform control so that an intensity of the sound wave of opposite phase outputted from the speaker weakens gradually after the controller determines, based on the sleep state, that a timing for awakening the user has been reached.

2. The electronic device of claim 1, wherein the controller is configured to cause the sound wave of opposite phase to be outputted from the speaker until the controller determines, based on the sleep state, that a timing for awakening the user has been reached.

3. The electronic device of claim 1, wherein the controller is configured to control, based on the sleep state, an intensity of the sound wave of opposite phase outputted from the speaker.

4. The electronic device of claim 1, wherein based on the sleep state, the controller is configured to cause an alarm sound to be outputted from the speaker to encourage the user to awaken.

5. The electronic device of claim 4, wherein the controller is configured to cause the alarm sound to be outputted when the controller determines, based on the sleep state, that a timing for awakening the user has been reached.

6. The electronic device of claim 5, wherein the controller is configured to gradually increase an intensity of the alarm sound outputted from the speaker after the controller determines, based on the sleep state, that the timing for awakening the user has been reached.

7. The electronic device of claim 1, further comprising a vibration unit capable of generating vibration, based on the sleep state, to encourage the user to awaken.

8. The electronic device of claim 1, wherein the sensor comprises an optical emitter capable of irradiating light on the measured part of the user, and an optical detector capable of detecting interference light that includes light scattered at the measured part.

9. A control system comprising:
a measurement apparatus comprising a speaker configured to output a sound wave, and a sensor configured to acquire an optical signal related to blood flow at a measured part of a user; and
a control apparatus comprising a controller configured to measure blood flow information of the measured part based on the optical signal, to estimate a sleep state of the user based on the blood flow information, and to control a sound wave outputted from the speaker based on the sleep state of the user,
wherein the measurement apparatus further comprises a microphone configured to collect an ambient sound wave; and
wherein the control apparatus is configured to control the sound wave outputted from the speaker based on the ambient sound wave and the sleep state of the user,
wherein the sound wave outputted from the speaker is a sound wave of opposite phase from the ambient sound wave; and
wherein the controller is configured to perform control so that an intensity of the sound wave of opposite phase outputted from the speaker weakens gradually after the controller determines, based on the sleep state, that a timing for awakening the user has been reached.

10. The control system of claim 9, wherein the control apparatus is configured to output an alarm sound from the speaker to awaken the user based on the sleep state.

11. A control method comprising:
acquiring an optical signal related to blood flow at a measured part of a user;
measuring blood flow information of the measured part based on the optical signal;
estimating a sleep state of the user based on the blood flow information;
performing control of a sound wave for output based on the sleep state; and
outputting the sound wave based on the control;
acquiring an ambient sound wave;
performing control of the sound wave for output based on the ambient sound wave and the sleep state,
wherein the outputted sound wave is a sound wave of opposite phase from the ambient sound wave; and
wherein the controller is configured to perform control so that an intensity of the outputted sound wave of opposite phase weakens gradually after the controller determines, based on the sleep state, that a timing for awakening the user has been reached.

12. The control method of claim 11, further comprising outputting an alarm sound to awaken the user based on the sleep state.

13. A non-transitory computer readable medium storing a control program for causing a computer to:
acquire an optical signal related to blood flow at a measured part of a user;
measure blood flow information of the measured part based on the optical signal;
estimate a sleep state of the user based on the blood flow information;
control a sound wave for output based on the sleep state; and
output the controlled sound wave,
collect an ambient sound wave; and
control the sound wave for output based on the ambient sound wave and the sleep state,
wherein the outputted sound wave is a sound wave of opposite phase from the ambient sound wave; and
wherein the controller is configured to perform control so that an intensity of the outputted sound wave of opposite phase weakens gradually after the controller determines, based on the sleep state, that a timing for awakening the user has been reached.

14. The non-transitory computer readable medium of claim 13, the control program further comprising causing the computer to output an alarm sound to awaken the user based on the sleep state.

* * * * *